United States Patent
Knowlson et al.

(10) Patent No.: US 10,415,166 B2
(45) Date of Patent: Sep. 17, 2019

(54) HYDROENTANGLED AIRLAID PROCESS AND INDUSTRIAL WIPE PRODUCTS

(71) Applicant: Jacob Holm & Sons AG, Basel (CH)

(72) Inventors: Richard Knowlson, Charlotte, NC (US); Eric Mariani, Richwiller (FR); Geoffrey William Collins, Witterswil (CH)

(73) Assignee: Jacob Holm & Sons AG, Basel (CH)

( * ) Notice: Subject to any disclaimer, the term of this patent is extended or adjusted under 35 U.S.C. 154(b) by 136 days.

(21) Appl. No.: 15/595,251

(22) Filed: May 15, 2017

(65) Prior Publication Data

US 2018/0326699 A1    Nov. 15, 2018

(51) Int. Cl.

| | |
|---|---|
| *D04H 1/425* | (2012.01) |
| *D04H 1/4374* | (2012.01) |
| *A61K 8/02* | (2006.01) |
| *D04H 1/492* | (2012.01) |
| *D04H 1/49* | (2012.01) |
| *D04H 1/54* | (2012.01) |
| *D04H 1/732* | (2012.01) |
| *D04H 1/4382* | (2012.01) |

(52) U.S. Cl.
CPC .......... *D04H 1/425* (2013.01); *A61K 8/0208* (2013.01); *D04H 1/4374* (2013.01); *D04H 1/49* (2013.01); *D04H 1/492* (2013.01); *D04H 1/54* (2013.01); *D04H 1/732* (2013.01); *D04H 1/4382* (2013.01)

(58) Field of Classification Search
CPC ........ A61K 8/0208; B32B 5/26; D04H 1/425; D04H 1/4374; D04H 1/4382; D04H 1/492
See application file for complete search history.

(56) References Cited

U.S. PATENT DOCUMENTS

| | | |
|---|---|---|
| 2002/0187307 A1 | 12/2002 | Tanaka et al. |
| 2004/0013859 A1 | 1/2004 | Annis et al. |
| 2006/0211323 A1 | 9/2006 | Benim et al. |
| 2014/0170402 A1 | 6/2014 | Knowlson et al. |

OTHER PUBLICATIONS

International Search Report with Search History and Written Opinion dated Jul. 3, 2018 in corresponding PCT/US2018/028564 filed Apr. 20, 2018.

*Primary Examiner* — Arti Singh-Pandey
(74) *Attorney, Agent, or Firm* — Oblon, McClelland, Maier & Neustadt, L.L.P.

(57) ABSTRACT

A method to prepare nonwoven webs suitable for use as an industrial wipe which have good MD and CD strength is provided. The method includes hydroentangling an airlaid web of natural cellulose fibers having a fiber length of no more than 3.5 mm, bonding fibers having a fiber length of from 6.0 to 12.0 mm and optionally, manmade fibers having a fiber length of from 6.0 to 12.0 mm. The airlaid web is a homogeneous mat of the natural cellulose fibers, the optional manmade fibers and the bonding fibers and is not laid on a precursor web. No non-fiber adhesive or binder is utilized. The airlayering and hydroentangling are conducted in a continuous operation. The method to manufacture the nonwoven web may include an embossing or crepeing operation.

23 Claims, 2 Drawing Sheets

HYDROENTANGLED AIRLAID PROCESS AND INDUSTRIAL WIPE PRODUCTS

FIELD OF THE INVENTION

This invention is directed to a continuous method for preparing nonwoven webs having high wet strength, abrasion resistance, solvent resistance, low or no linting or dusting and good absorbency which are suitable for use as an industrial disposable wipe.

BACKGROUND OF THE INVENTION

Industrial wipes are disposable non oven products used for a variety of applications in industry and institutions, including food service wipes, general industrial, specialty wipes and medical wipes. These products can be wet or dry and may be impregnated with ingredients for specific purposes, such as polishing, cleaning, or removing bacteria. As a result of the desire for convenient, time saving, easy to use products that are economically efficient and prevent cross-contamination there is an ongoing need for single or limited-use industrial and institutional wipes which meet the performance and economy sought by the target end use and processes to produce them which are economical and energy efficient.

Nonwoven wipes, whether intended for consumer application or industrial application may be engineered to provide products of high strength, good abrasion resistance and good hygiene which have no residual oils or contaminants such as heavy metals. Utilities for an industrial wipe may include cleaning machinery, tools, floors and facilities, absorbing fluids and oil, personal cleaning and hygiene, polishing and dust removal.

Conventionally, nonwoven disposable wipe products have been produced through a wide range of industrial methods which are known to one of skill in the art. Generally, although each manufacturer employs technical variation in order to obtain nonwoven webs of specific target properties, the conventionally most common methods employed may be categorized broadly by the terms airlaid, spunlacing, double recrepe, airlacing and hydroentangled co-form.

Basic airlaid webs are composed of fibers dry laid on a forming web. In order to obtain strength most airlaid nonwovens are bonded with latex binder compositions or multibonded with bicomponent adhesive fibers and latex. Airlaid webs may offer advantage by use of low cost and biodegradable raw material (wood pulp), but also include non-biodegradable and expensive latex binder and bicomponent fibers. As a result, depending on the binder and/or bicomponent fiber content the nonwoven may be stiff or have only moderate dry/wet strength and abrasion resistance.

According to the "hydraspun" method as described in U.S. Pat. No. 4,755,421 to Manning et al. a wetlaid web of pulp and manmade fibers is hydroentangled in a spunlacing operation and dried. However, such products may suffer from poor wet strength which is typically compensated with the addition of non-biodegradable binders. U.S. Pat. No. 7,732,357 to Annis et al. describes the use of binder fibers to the nonwoven sheet that upon heating become activated by at least partial melting and form fiber to fiber bonds. Accordingly, depending on the fiber composition which may generally contain a high content of staple manmade fiber and bicomponent fiber, spunlace webs may be expensive or if bonding fibers are not present or of low content the nonwoven web may suffer from low strength, low abrasion resistance and poor dimensional stability.

In a double recrepe process (DRC), a base sheet is creped, then printed with a latex binder on one side of the base sheet. The printed base sheet is creped again, then printed with a binder on the other side of the base sheet, followed by creping the base sheet a third time. The DRC process provides a web possessing a good combination of strength and softness, but has lower strength, and abrasion resistance and includes a non-biodegradable latex binder.

Airlace methods generally include a combination of airlayering and then spunlacing the web. Conventionally, a precursor or base nonwoven web of staple manmade fibers is first produced, then an airlaid web of pulp fibers is deposited on it. The two webs are entangled in the spunlacing operation.

Airlace methods combine the operations of depositing an airlaid web of staple length fibers and wood pulp fibers onto a nonwoven carrier layer or precursor base nonwoven web and hydroentangling the airlaid layer with the nonwoven carrier. This technology is described in U.S. Pat. No. 8,250,719 to Ouellette and the references described therein. In addition to employing a carrier web, Ouellette describes bonding the airlaid fibers with hot air or a spray adhesive.

Hydroentangled co-formed webs are prepared by preforming at least two fibrous layers and hydroentangling the layers. The components of the co-formed mixture generally include wood pulp and thermoplastic filaments.

There remains a need for a method to prepare a nonwoven web suitable for use as an industrial wipe that has good dry/wet strength properties, high absorbency, low or no lint or dust content and having a good feel to the user.

Thus, an objective of the present invention is to provide a method to produce a nonwoven web that includes minimal processing operations, does not use adhesives or binders and provides a nonwoven web having sufficient wet tensile strength and absorbency for use as an industrial wipe. Another objective of this invention is to provide a nonwoven web having sufficient wet strength and absorbency to be employed as an industrial wipe.

SUMMARY OF THE INVENTION

These and other objectives have been achieved according to the present invention, the first embodiment of which includes a method for production of a nonwoven web, comprising: preparing a mixture of defibrated natural cellulose fibers, bonding fibers and optionally, manmade fibers; airforming the mixture to obtain at least one homogeneous airlaid web; hydroentangling the airlaid web to consolidate the web on at least one side; and drying and thermobonding the hydroentangled web to obtain the nonwoven web; wherein the airforming and hydroentangling is conducted in a continuous operation, a content of the natural cellulose fibers in the mixture of fibers is from 50 to 90% by weight, a content of the bonding fibers and optional manmade fibers is from 10 to 50% by weight, no non-fiber binder or adhesive is utilized, no continuous fiber is utilized, a fiber length of the natural cellulose fibers is no more than 3.5 mm, a fiber length of the bonding fibers is from 6.0 to 12.0 mm, a fiber length of the optional manmade fibers is from 6.0 to 12.0 mm, a basis weight of the nonwoven web is from 20 g/m$^2$ to 100 g/m$^2$, a thickness of the nonwoven web is from 0.25 mm to 2 mm, and the % by weight is relative to a total dry weight of the nonwoven web.

In an aspect of the first embodiment, the airlaid web is directly formed on a carrier of the airformer without preforming a precursor web or incorporating a continuous filament web.

In an aspect of the first embodiment the content of the bonding fiber is from 10 to 20% by weight of the dry nonwoven web.

In a further aspect, the first embodiment includes embossing the hydroentangled web; wherein the embossing operation is continuous with the airforming and hydroentangling.

In an additional further aspect the first embodiment includes mechanical crepeing of the dried hydroentangled web.

In another embodiment, the present invention provides a nonwoven web obtained by the method according to the first embodiment, wherein a CD wet tensile strength of the nonwoven web is at least 1.8 lbf (8 N/5 cm) and a MD/CD ratio is less than 3.

In a special aspect the nonwoven web comprises: from 60% to 85% by weight of wood pulp; from 20% to 5% by weight of lyocell; and from 10 to 20% by weight bonding fibers; wherein the basis weight of the nonwoven web is from 40 g/m$^2$ to 60 g/m$^2$, a MD/CD ratio is less than 3, a CD wet tensile strength is at least 2.7 lbf (12 N/5 cm), and the thickness of the nonwoven web is from 0.5 mm to 1.5 mm.

In a further special aspect, the nonwoven web comprises: from 60% to 85% by weight of wood pulp; from 20% to 5% by weight of viscose; and from 10 to 20% by weight bonding fibers; wherein the basis weight of the nonwoven web is from 40 g/m$^2$ to 60 g/m$^2$, a MD/CD ratio is less than 3, a CD wet tensile strength is at least 2.7 lbf (12 N/5 cm), and the thickness of the nonwoven web is from 0.5 mm to 1.5 mm.

The foregoing paragraphs have been provided by way of general introduction, and are not intended to limit the scope of the following claims. The described embodiments, together with further advantages, will be best understood by reference to the following detailed description taken in conjunction with the accompanying drawings.

DETAILED DESCRIPTION OF THE INVENTION

Figure 1:
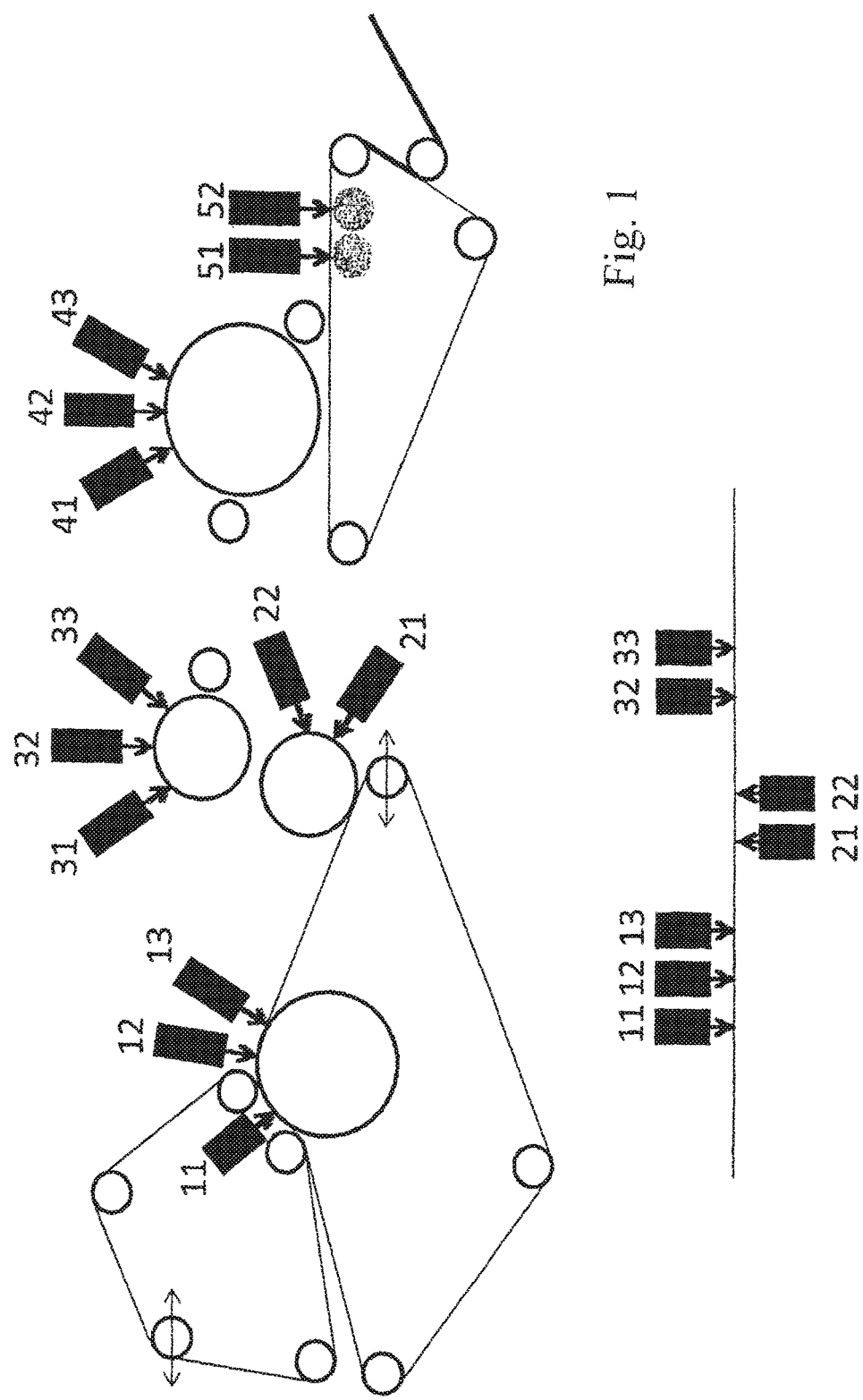
FIG. 1 shows a schematic drawing of an arrangement of water jets in a hydroentanglement unit according to one embodiment of the invention.

According to the following description, all numerical ranges described include all sub-ranges and all values there between unless otherwise specified. All weight content values are based on total weight. The following description provides a general description of the present invention and specific preferred embodiments. However, one of ordinary skill will recognize that many variations of the invention may be possible without departing from the gist of the invention. This description and the following Claims are intended to include all such variation.

In a first embodiment, the present invention provides a method for production of a nonwoven web, comprising: preparing a mixture of defibrated natural cellulose fibers, bonding fibers and optionally, manmade fibers; airforming the mixture to obtain at least one homogeneous airlaid web; hydroentangling the airlaid web to consolidate the web on at least one side; and drying and thermobonding the hydroentangled web to obtain the nonwoven web; wherein the airforming and hydroentangling is conducted in a continuous operation, a content of the natural cellulose fibers in the mixture of fibers is from 50 to 90% by weight, a content of the bonding fibers and optional manmade fibers is from 10 to 50% by weight, no non-fiber binder or adhesive is utilized, no continuous fiber is utilized, a fiber length of the natural cellulose fibers is no more than 3.5 mm, a fiber length of the bonding fibers is from 6.0 to 12.0 mm, a fiber length of the optional manmade fibers is from 6.0 to 12.0 mm, a basis weight of the nonwoven web is from 20 g/m$^2$ to 100 g/m$^2$, a thickness of the nonwoven web is from 0.25 mm to 2 mm, and the % by weight is relative to a total dry weight of the nonwoven web.

The length of the natural cellulose fibers is no more than 3.5 mm, preferably 1.5 mm to 3.5 mm, most preferably 2.5 to 3.5 mm. Any natural cellulose fiber may be employed as the short fiber of the mixture. In one embodiment a wood pulp of the described length may be the short fiber and in a preferred embodiment, a southern pine Kraft may be the natural cellulose fiber. Wood pulp obtained from a sulfite pulping process may additionally be the source of the natural cellulose fibers. Mixtures of natural cellulose fibers may be used. The natural cellulose fibers may be defibrated to form a mixture of individual loose fibers.

Defibrated fibers are wood fibers obtained in a dry hammermill type operation which is known to one of skill in the art. In the hammermill treatment the wood pulp is defribrated into individual fibers which are airborne and dispersed in the air flow which carries the dry individual fibers to an airlayering operation. Good dispersion and effective deagglomeration of the pulp may be important to the formation of an air-laid web.

The manmade fibers may be any non-thermoplastic fiber or mixture of fibers which is conventionally employed in the production of nonwoven webs in the wiper industry. Such fibers include synthetic fibers such as for example, but not limited to polyester fibers and polypropylene fibers. One of skill in the art may select a synthetic fiber or fiber combination to obtain specific target properties of the web. In an aspect of the invention the manmade fibers may be sustainable materials derived from base raw materials obtained from renewable sources such as a rotational crop or an animal produced material. The base raw material may be modified as in the case of cellulose acetate. Examples of sustainable fiber materials include but are not limited to cellulose acetate, polylactic acid, esters of polylactic acid, amides of polylactic acid, lyocell, viscose and milk protein. Preferably the manmade fiber is viscose or lyocell. Mixtures of these sustainable fibers or mixtures of synthetic and sustainable fibers may be employed.

As familiar to one of skill in the art, synthetic and manmade fibers may be obtained in a variety of cross sectional shapes. For example, conventionally known cross sectional shapes may include circular, flat, trilobal and X shaped, each may have differing degrees of crenelation or surface irregularity or waviness depending upon the chemistry and method of production of the fiber. As surface to surface interaction may contribute to the strength and structural properties of the nonwoven web, one of skill will recognize that the cross-sectional shape may be selected to vary the degree of stiffness, surface area available for bonding and degree of water absorbency of the nonwoven web.

According to the embodiments of the present invention the length of the manmade fiber or fibers of the nonwoven web may be no less than 6.0 mm, preferably 6.0 to 25 mm, most preferably 6.0 mm to 12 mm in length.

In one embodiment the manmade sustainable fibers may be viscose fibers such as marketed under the tradenames DANUFIL®, VILOFT® and GALAXY® by Kelheim Fibres. These commercially available fibers are identified only as example materials and are not intended to be limiting.

The bonding fibers may be any such as known to one of ordinary skill in the art. Preferably the bonding fibers are composed of a core and sheath structure wherein the sheath contains or is made of a polymer having a melting point lower than the melting point of the polymer or polymer composition of the core. In this way it is possible to selectively melt or soften the sheath to bond with other fibers while the integrity of the fiber is retained by the non-melted core. The melting range of the bonding fiber may be set to be within the temperature range of the drying unit so that drying and thermobonding take place at virtually the same time. In one preferred aspect the bonding fiber may have a polypropylene or polyester core and the sheath may be polyethylene or polyester low melt (PLM). Such bicomponent fibers may be engineered to provide variation of sheath melting temperature for bonding purposes while imparting three dimensional structure to the nonwoven fiber matrix.

The content of bonding fiber in the nonwoven web composition may be from 5 to 25% by weight, preferably 8 to 20% by weight and most preferably 10 to 16% by weight. As understood by one of skill in the art many of the properties of the nonwoven web may adjusted by variation of the bonding fiber content and therefore, in certain embodiments of the present invention the bonding fiber content may not be within the preferred and most preferred ranges listed in this paragraph.

The method of forming an air laid web is generally described in U.S. Pat. No. 4,640,810 to Laursen et al. The defibrated natural cellulose fibers, bonding fibers and manmade fibers, if present, are blended to a homogeneous mixture and while supported in an air stream, transported to a distributor unit. The distributor unit contains a rotating cylinder or drum that is perforated with holes, slots or other appropriately shaped apertures designed to allow passage of the fibers onto a foraminous carrier. The construction of the drum and configuration and size of the apertures may be varied according to the characteristics of the fiber mixture to be employed and to obtain unique web construction. Under the influence of a combination of any of air flow, mechanical agitation within the drum and suction from beneath the carrier, the fibers are directed through the openings of the perforated drum and form a homogeneous web on the surface of the carrier. The height and degree of matting of the dry web may be varied via control of process variables including fiber content and size, drum aperture size and shape, rate of air flow, degree of suction applied from the bottom of the carrier and carrier speed. Other equipment controls may also be varied to provide unique matting construction. By air laying the mat as a homogeneous dry mixture of the defibrated natural cellulose fibers, bonding fibers and manmade fibers, if present, a single homogeneous layer of the component fibers may be obtained.

The width of the web depends upon the type of air former equipment employed and may vary from 1 m to 6 m. Conventional commercial units such as supplied by Dan-Web, Oerlikon and Anpap Oy range from 2 to 5 m in width.

According to the present invention the formed air laid web is directly and continuously transported to a hydroentanglement unit or spunlacing unit, where the airlaid homogeneous mat is struck with a series of high pressure water jets to mechanically entangle or consolidate the fibers and form the nonwoven web. The jets may be oriented perpendicular to the surface of the carrier or angled to provide unique properties to the web. Jets may be placed to consolidate the web from one side, preferably, the top side or from both the top and bottom side. The pressure of the jets may be from 0.07 bars/kg/h/m to 11 bars/kg/h/m, preferably, 0.1 bars/kg/h/m to 10 bars/kg/h/m, and most preferably 1.0 bars/kg/h/m to 3 bars/kg/h/m.

An embodiment showing an arrangement of jets to consolidate a web from both sides is shown schematically in FIG. 1. As indicated by FIG. 1, the air laid web taken directly from the airformer is passed along a series of carrier belts and exposed to high pressure jets indicated in numerical order. Jets 11, 12 and 13 impinge the top of the web while jets 21 and 22 strike the opposite or bottom side. The schematic jets 11-13, 21-22, 31-33, 41-43 and 51-52 represent banks of jets across the width of the web and the jet banks may be positioned and arranged to impart varying completeness of entanglement across the web. Thus the entanglement may be patterned or random depending on the intended end use of the nonwoven web.

The drape, softness, comfortable hand of the nonwoven web may be controlled by the energy delivered by the high pressure jets and by the speed of travel of the web through the equipment. Additionally, the porosity and absorbency of the nonwoven web may be affected by these parameters along with the content and structure of the bonding fibers. According to the present invention by control of both water pressure and speed of web travel through the spunlacing equipment, the composition make-up of natural cellulosic fibers, manmade and bonding fibers as well as the absence of adhesives and binders, a nonwoven web having varying degrees of strength, absorbency, softness and thickness may be obtained. Further, the bonded nonwoven web is free on adhesives and binders it is hygienically safe and substantially free of lint and dust particles.

Spunlacing or hydroentanglement units are available from Fleissner GmbH (Germany) and Andritz Perfojet (France).

Figure 2:
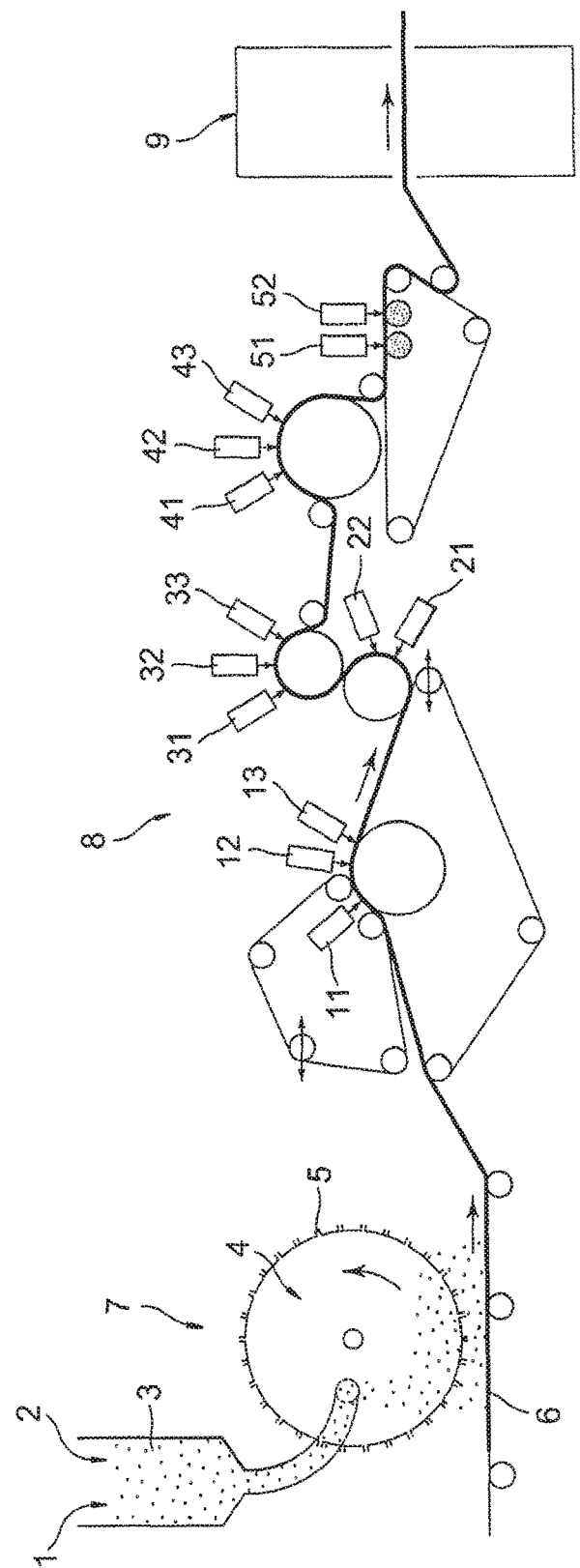
FIG. 2 shows a schematic diagram of the continuous production line of an embodiment of the invention.

FIG. 2 shows a schematic drawing of an embodiment of a continuous system for preparing the hydroentangled airlaid web. The airforming system is shown as unit (7), wherein the defibrated natural cellulose fibers (1) and bonding fibers optionally including the manmade fibers (2) are homogeneously mixed in supply unit (3) and then transferred into rotating cylinder (4) having perforations (5). The mixture of defibrated natural cellulose fibers, manmade fibers, if present, and bonding fibers pass through the perforations onto the foraminous carrier (6) which transports the airlaid web through the hydroentangling unit (8) as described above. From the unit (8) the consolidated web is dried an thermobonded in drying unit (9).

In one variation of the above basic embodiment, multiple airlaid homogeneous webs as previously described may be prepared and stacked prior to spunlacing so that thicker nonwoven webs may be produced. The respective stacked layers may be of the same fiber composition or may have differing compositions selected for the intended end use of the nonwoven web. In each such possible embodiment, entanglement may be achieved by variation of water jet pressure and speed of travel of the web through the spunlacing unit. No non-fiber binders or adhesives are utilized.

Following the spunlacing the wet nonwoven web may be dried and wound for transport and storage. In further preferred aspect the nonwoven mat may be embossed. According to this aspect the embossing may take place prior to the drying operation in which case a hydroembossing operation may be employed. Alternatively, the hydroentangled web may be embossed after the drying and thermobonding operation in which case embossing may be accomplished by thermal embossing. Any of the conventional methods for hydroembossing or thermoembossing may be employed and special and unique effects with regard to appearance, increased strength, feel and absorbency may be obtained by application of these methods. One of skill in the art may determine the effects and parameters via standard experimentation.

In another alternative aspect, the dried hydroentangled and thermally bonded web may be mechanically creped in order to increase the softness of the web, increase the bulk of the web and/or to impart surface structure to the dried bonded web. Any of creping units with different blade configuration may be applied to obtain varying degrees of softness and bulk. In order to have the nonwoven web crepped it may be necessary to slit the web to a shorter width.

Any of commercially available crepeing units may be employed, such as for example, units available form Micrex®.

The basis weight of the nonwoven web may be from 20 $g/m^2$ to 100 $g/m^2$, preferably, 40 $g/m^2$ to 80 $g/m^2$ for a nonwoven web of from 0.25 mm to 2 mm in thickness. However, when multiple airlaid webs are stacked, the basis weight and thickness may not be in these ranges. Basis weight may be varied by control of the process variables described for both the airlaying and spunlacing operations and by other process variables conventionally known to one of skill in the present technology.

The nonwoven webs according to the present invention have strength profiles which are more omnidirectional than some conventionally available nonwoven webs. The ratio of the wet tensile strength in the machine direction (MD) to the cross machine direction (CD) is less than 3, preferably less than 2 and most preferably the CD/MD tensile strength ratio is from 1.5 to 1.0.

In one select embodiment, the nonwoven web may comprise: from 60% to 85% by weight of wood pulp; from 20% to 5% by weight of lyocell; and from 10 to 20% by weight bonding fibers; wherein the basis weight of the nonwoven web is from 40 $g/m^2$ to 60 $g/m^2$, a MD/CD ratio is less than 3, a CD wet tensile strength is at least 2.7 lbf (12 N/5 cm), and the thickness of the nonwoven web is from 0.5 mm to 1.5 mm.

In another select embodiment the nonwoven web may comprise: from 60% to 85% by weight of wood pulp; from 20% to 5% by weight of viscose; and from 10 to 20% by weight bonding fibers; wherein the basis weight of the nonwoven web is from 40 $g/m^2$ to 60 $g/m^2$, a MD/CD ratio is less than 3, a CD wet tensile strength is at least 2.7 lbf (12 N/5 cm), and the thickness of the nonwoven web is from 0.5 mm to 1.5 mm.

The nonwoven webs according to the present invention may be particularly suitable as industrial wipes for any of the utilities described above, wherein dry and wet strength, absorbency, hygiene and low dust and/or lint content are required. Thus in another embodiment the present invention provides an industrial wipe which may be in the form of rolls, sheets, folded sheets or compressed in dispensing units.

Depending on the intended function and utility of the industrial wipe at least one selected from the group consisting of a solvent, a cleansing agent, a sterilizing agent, a deodorizing agent, a disinfectant, a polishing agent and an anti-static agent may be contained in the nonwoven web.

EXAMPLES

A homogeneous mixture of defibrated natural cellulose fibers, lyocell and bicomponent bonding fibers was airlaid, hydroentangled and dried/thermobonded according to Claim 1. The first sample was tested as Sample A-Flat. A second sample was prepared by mechanically crepeing the Sample A-Flat web to produce a nonwoven Sample A-Creped. The two samples were then tested and compared to commercially available wipes as listed in Table I. As shown in Table I the nonwoven webs according to the present invention have a basis weight and tensile strength intermediate to the range of values of the commercial wipe products tested. However, unexpectedly the products according to Claim 1 show higher relative water absorbency.

| SAMPLE ID | Company | Basis Wt. (opsy) | Basis Wt. (gsm) | Thickness mils | Grabs MD Max Load (lbf) | Grabs XD Max Load (lbf) | Wet Grabs MD Max Load (lbf) | Wet Grabs XD Max Load (lbf) |
|---|---|---|---|---|---|---|---|---|
| A-Flat (80/10/10) | JHI | 1.75 | 59.33 | 23.00 | 8.05 | 4.90 | 4.34 | 3.09 |
| A-Crepped (80/10/10)) | JHI | 1.77 | 60.00 | 22.17 | 7.19 | 4.81 | 3.80 | 2.80 |
| B-Flat (80/20 Bico) | JHI | 1.75 | 59.33 | 21.50 | 7.80 | 5.68 | 3.48 | 2.65 |
| B-Crepped (80/20 Bico) | JHI | 1.86 | 63.05 | 20.3 | 6.9 | 5.2 | 2.9 | 2.4 |
| KCL40 | Kimberly Clark | 2.17 | 73.68 | 14.58 | 3.39 | 4.96 | 1.67 | 2.21 |
| KC X50 | Kimberly Clark | 1.45 | 49.16 | 15.93 | 9.51 | 5.98 | 6.41 | 4.65 |
| KC X60 | Kimberly Clark | 1.83 | 62.15 | 15.33 | 11.71 | 6.50 | 8.08 | 5.23 |
| 8838 | Sontara | 1.49 | 50.51 | 9.60 | 29.62 | 13.45 | 21.90 | 9.64 |
| K838 | Sontara | 1.55 | 52.6 | 14.5 | 24.81 | 15.51 | 20.61 | 11.81 |

| SAMPLE ID | % ABS Di water (Strip absorbency) | % ABS Motor Oil (Strip absorbency) | Absorbent Capacity (GATS) % | Absorbent Capacity GATS ($g/m^2$) | Wet taber(wt loss) mg | Absorbency rate (GATS Rate @ 80%) |
|---|---|---|---|---|---|---|

-continued

| | | | | | | |
|---|---|---|---|---|---|---|
| A-Flat (80/10/10) | 848.60 | 923.69 | 637.00 | 378.03 | 77.00 | 0.59 |
| A-Crepped (80/10/10)) | 829.38 | 888.39 | 606.00 | 363.48 | 83.00 | 0.52 |
| B-Flat (80/20 Bico) | 843.45 | 911.62 | 668.00 | 396.21 | 81.00 | 0.64 |
| B-Crepped (80/20 Bico) | 840.8 | 887.04 | 585.0 | 369.05 | 89.00 | 0.48 |
| KCL40 | 699.00 | 1074.75 | 431.00 | 332.13 | **** | 0.23 |
| KC X50 | 631.00 | 1140.75 | 661 | 324.83 | 50.00 | 0.24 |
| KC X60 | 550.00 | 887.80 | 516 | 320.13 | 75.00 | 0.25 |
| 8838 | 420 | 930 | 397 | 202.00 | 15.00 | 0.17 |
| K838 | 470 | 947 | 501 | 271.63 | 37.00 | 0.31 |

(Load values stated in lbf can be converted to N/5 cm by multiplying lbf by a factor of 4.45)

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A method for production of a nonwoven web, comprising:
   preparing a mixture of defibrated natural cellulose fibers, bonding fibers and optionally, man made fibers;
   airforming the mixture to obtain at least one homogeneous airlaid web;
   hydroentangling the airlaid web to consolidate the web on at least one side; and
   drying and thermobonding the hydroentangled web to obtain the nonwoven web;
   wherein
   the airforming and hydroentangling is conducted in a continuous operation,
   a content of the natural cellulose fibers in the mixture of fibers is from 50 to 90% by weight,
   a content of the bonding fibers and optional manmade fibers is from 10 to 50% by weight,
   no non-fiber binder or adhesive is utilized,
   no continuous fiber is utilized,
   a fiber length of the natural cellulose fibers is no more than 3.5 mm,
   a fiber length of the bonding fibers is from 6.0 to 12.0 mm,
   a fiber length of the optional manmade fibers is from 6.0 to 12.0 mm,
   a basis weight of the nonwoven web is from 20 g/m² to 100 g/m²,
   a thickness of the nonwoven web is from 0.25 mm to 2 mm, and
   the % by weight is relative to a total dry weight of the nonwoven web.

2. The method according to claim 1 wherein the basis weight is from 40 g/m² to 60 g/m².

3. The method according to claim 1, wherein the manmade fiber is present and the manmade fiber comprises at least one of a synthetic polymer and a sustainable polymer.

4. The method according to claim 3 wherein the natural cellulose fiber is wood pulp and the manmade fiber is viscose or lyocell.

5. The method according to claim 1, wherein the bonding fiber is a bicomponent fiber having a sheath of a polymer and a core of at least one polymer different from the sheath polymer; wherein a melting point of the sheath polymer is less than a melting point of the at least one polymer of the core.

6. The method according to claim 5 wherein the sheath of the bonding fiber comprises at least one of polyethylene or PLM and the core of the bonding fiber comprises at least one of a polypropylene and a polyester.

7. The method according to claim 1, wherein a content of the bonding fiber is from 8 to 25% by weight of the dry nonwoven web.

8. The method according to claim 4, wherein the wood pulp is a sulfite pulp obtained by sulfite pulping.

9. The method according to claim 1 wherein the airlaid web is hydroentangled to consolidate the web on both sides.

10. The method according to claim 1 wherein an applied pressure of the hydroentanglement is from 0.07 bars/kg/him to 11 bars/kg/h/m.

11. The method according to claim 10 wherein the applied pressure of the hydroentanglement is from 1.0 bars/kg/h/m to 3 bars/kg/h/m.

12. The method according to claim 5 wherein a temperature of the drying operation is equal to or up to 10° C. greater than the melting point of the sheath polymer with the proviso that the drying temperature is less than the melting point of the at least one core polymer.

13. The method according to claim 1, further comprising:
   embossing the hydroentangled web; wherein the embossing operation is continuous with the airforming and hydroentangling.

14. The method according to claim 1, further comprising crepeing the dried and thermobonded nonwoven web.

15. The method according to claim 1, wherein the airforming of the airlaid web is conducted in a single airformer.

16. The method according to claim 1, wherein the airforming of the airlaid web is conducted in more than one airformer and the fiber content of each web is the same.

17. The method according to claim 1, wherein the airforming of the airlaid web is conducted in more than one airformer and a fiber content of at least one web is different from the fiber content of another web.

18. The method according to claim 1, wherein the airlaid web is directly formed on a carrier of the airformer without preforming a precursor web or incorporating a continuous filament web.

19. The method according to claim 1, wherein a ratio of tensile strength in a machine direction to tensile strength in a direction perpendicular to the machine direction (MD/CD) is less than 3.

20. A nonwoven web obtained by the method according to claim 1, wherein
 a CD wet tensile strength of the nonwoven web is at least 8 N/5 cm and a MD/CD ratio is less than 3.

21. The nonwoven web according to claim 20, wherein the nonwoven web comprises:
 from 60% to 85% by weight of wood pulp;
 from 20% to 5% by weight of lyocell; and
 from 10 to 20% by weight bonding fibers; wherein the basis weight of the nonwoven web is from 40 g/m$^2$ to 60 g/m$^2$, a MD/CD ratio is less than 3, a CD wet tensile strength is at least 12 N/5 cm, and the thickness of the nonwoven web is from 0.5 mm to 1.5 mm.

22. The nonwoven web according to claim 20, wherein the nonwoven web comprises:
 from 60% to 85% by weight of wood pulp;
 from 20% to 5% by weight of viscose; and
 from 10 to 20% by weight bonding fibers;
 wherein the basis weight of the nonwoven web is from 40 g/m$^2$ to 60 g/m$^2$ a MD/CD ratio is less than 3, a CD wet tensile strength is at least 12 N/5 cm, and the thickness of the nonwoven web is from 0.5 mm to 1.5 mm.

23. An industrial wipe, comprising:
 the nonwoven web according to claim 20; and
 at least one selected from the group consisting of a solvent, a cleansing agent, a sterilizing agent, a deodorizing agent, a disinfectant, a polishing agent and an anti-static agent.

* * * * *